United States Patent [19]
Crawford et al.

[11] Patent Number: 4,606,004
[45] Date of Patent: Aug. 12, 1986

[54] APPARATUS FOR REDUCTION OF FILTRATION TRUNCATION ERRORS

[75] Inventors: Carl R. Crawford, Milwaukee; Kishore C. Acharya, West Allis, both of Wis.

[73] Assignee: General Electric Company, Milwaukee, Wis.

[21] Appl. No.: 591,730

[22] Filed: Mar. 21, 1984

[51] Int. Cl.⁴ .............................................. G06F 15/42
[52] U.S. Cl. ...................................... 364/414; 382/43; 382/6; 378/901
[58] Field of Search .................. 382/43; 364/414, 421, 364/728, 724; 358/167, 39

[56] References Cited
U.S. PATENT DOCUMENTS

| 4,283,767 | 8/1981 | Roundtree | 364/517 |
| 4,511,922 | 4/1985 | Lewis | 358/166 |
| 4,550,371 | 10/1985 | Glover | 364/414 |

Primary Examiner—Jerry Smith
Assistant Examiner—B. Hayes
Attorney, Agent, or Firm—Alexander M. Gerasimow; Douglas E. Stoner

[57] ABSTRACT

Apparatus for reduction of filtration truncation errors caused by convolving a plurality of input signals, such as line-integral projection data obtained in a computerized tomography (CT) scan of an object, with a common kernel function in a finite precision machine using Fourier transform techniques. The resulting convolved output signals contain correlated noise which, in the case of reconstructed CT images, manifests itself as structured noise in the form of rings and center spots in the image. The correlated noise can be reduced by randomly shifting the data prior to convolving it. The random shift can be achieved by a rotational permutation scheme. Another scheme for shifting the data is to prepend or append zeros to the data by using a random number generator or a deterministic function.

36 Claims, 4 Drawing Figures

APPARATUS FOR REDUCTION OF FILTRATION TRUNCATION ERRORS

BACKGROUND OF THE INVENTION

This invention relates to an improved apparatus for reconstructing a two-dimensional image of an object slice from linear projection data. More specifically, the invention relates to reconstruction of images which are free from artifacts due to filtration truncation errors.

The preferred embodiments of the invention will be described with reference to X-ray projection data obtained using transmission computerized tomography (CT). The invention, however, is not so limited and may be practiced with data obtained by other suitable methods such as ultrasonic scanning, computed emission tomography, and nuclear magnetic resonance. Moreover, the invention is not limited to data obtained by medical diagnostic apparatus, but is applicable to data obtained by any method where errors result from truncation of data.

In medical diagnostic applications, the projection data obtained by any of the aforementioned modalities are processed with the aid of digital-processor means in accordance with basic techniques well known to the art to produce the desired images. A preferred image reconstruction technique utilized in CT employs convolution and backprojection of the data. A detailed description of this and other suitable reconstruction techniques is provided by R. A. Brooks and G. Di Chiro in "Principles of Computer-Assisted Tomography (CAT) and Radiographic and Radioisotopic Imaging," Phys. Med. Biol., Vol. 21, No. 5, pp. 689–732, 1976.

Briefly, in one preferred embodiment of a scan geometry utilized in CT, the X-ray source is mounted on a scanner base that is journalled for rotation about the nominally horizontal axis on a tiltable gantry. A multiple-cell X-ray detector is mounted on a scanner base on the opposite side of the axis from the X-ray source. The X-ray beam emanating from the source is collimated into a fan-shaped configuration that spreads over the circumferential length of the detector and is fanned in the direction to which the rotational axis of the scanner base is perpendicular. The patient to be examined is customarily supported on an X-ray-transmissive table top or cradle in coincidence with the rotational axis of the scanner. In the course of an examination, the X-ray source and detector orbit jointly about the patient so that the detector will be able to produce signals (referred to as raw data) representative of X-ray beam attenuated by the patient for a multiplicity of paths between the X-ray source and detector. The detector signals are sampled during a scan, such that at a given time all of the sampled detector outputs are referred to as either a projection or a view. The signals representative of beam attenuation are acquired by a data acquisition system and variously processed and backprojected to yield digital data representative of the intensity of the picture elements that comprise the image of the body layer that has been scanned. The picture element data is converted to analog video signals and is used to display the image on a video monitor.

The processing of the raw data prior to backprojection can be divided into a preprocessing step and a filtration step. The raw attenuation data is preprocessed to provide line-integral projection data. The preprocessed data is then also typically filtered by one of various methods described in the above-referenced article.

A preferred filtering operation requires convolving the preprocessed projection data with a kernel function prior to the operation of backprojection to create an image. The application of convolution to the image reconstruction process is disclosed in detail in U.S. Pat. No. 4,149,248, issued Apr. 10, 1979 to Pavkovich and which is assigned to the same assignee as the present invention. This patent is incorporated herein by reference as background information.

Typically, the convolution operation is implemented by taking the discrete Fourier transform (DFT) of the preprocessed projection data, multiplying it by the DFT of the kernel function, and, finally, obtaining the filtered projection data by taking the inverse DFT (IDFT) of the product. It should be noted that DFT's are performed using a fast Fourier transform algorithm commonly denoted FFT.

The projection preprocessing and the filtration operations are implemented using what will be referred to as a high-precision array processor. Such an array processor uses, for example, a 38-bit floating point number representation with 28 of the 38 bits used to represent the mantissa. In some CT system configurations, it is desirable to perform the preprocessing operations in one array processor and to perform the filtration operations in a second array processor. The second array processor can be optimized for DFT's using, for example, a 22-bit floating point representation with a 16-bit mantissa. Because of the reduced accuracy of the second processor, when compared to the high-precision processor, the resulting filtered projection data contains what will be referred to as filtration truncation errors. The truncation errors arise due to the decreased number of bits used to represent the mantissa in the lower precision processor. The effects of truncation errors have been reviewed, without suggesting a solution in accordance with the invention, in A. V. Oppenheim and R. W. Schafer, "Digital Signal Processing," Prentice-Hall, 1975.

Structured or correlated noise appears in the filtered projection data because similar truncation errors are made when filtering each preprocessed projection. The backprojection process enhances the projection-to-projection correlated noise, thus causing structured noise such as rings and center spots in the image.

It is, therefore, a principal object of the invention to provide a method to reduce the errors caused by truncation in a limited precision array processor when using it to convolve data using Fourier techniques.

SUMMARY OF THE INVENTION

An inventive apparatus for convolving a plurality of input signals with a common kernel by taking the inverse discrete Fourier transform (IDFT) of the product of the discrete Fourier transform (DFT) of each of the input signals with the DFT of a common kernel using a finite precision machine. As a result of using the finite precision machine, the resulting convolved signals have correlated noise. In the preferred embodiment, the input signals can be projection measurements obtained using a CT apparatus.

The apparatus includes means for obtaining the DFT of each input signal and means for obtaining a product of the DFT of each of the signals and the DFT of the kernel. The convolved signals are obtained by taking the IDFT of the product. The apparatus further includes means for performing a rotational permutation operation on each of said input signals prior to taking the DFT's thereof. The degree of rotational permutation is selectively variable for each of the input signals.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
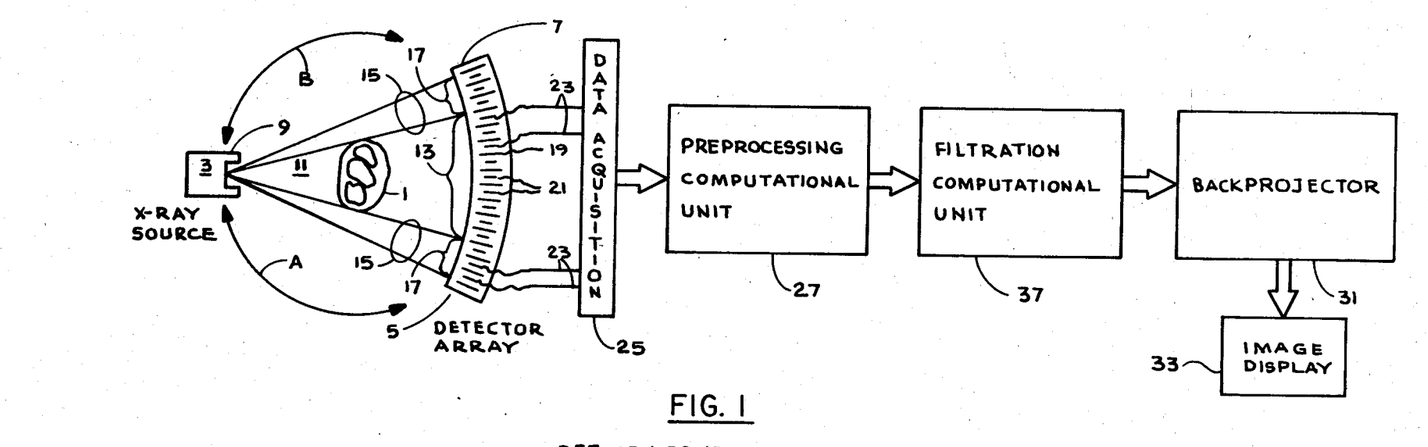
FIG. 1 is a schematic representation of a computerized tomography system with respect to which the preferred embodiment of the invention is disclosed.

Referring to FIG. 1, there is shown schematically a transmission-computed tomography apparatus utilizing a fan-beam scan geometry. A body 1 undergoing examination is interposed between an X-ray source 3 and an array of X-ray detectors, generally designated 5, supported in a detector housing 7. In a typical system, the detector housing may, for example, be filled with an ionizable gas, such as xenon, at a high pressure to increase the X-ray stopping power thereof. X-ray source 3 typically includes a collimation means 9 which functions to confine the X-ray energy emanating from the source to a substantially planar, fan-shaped beam 11. A central sector of X-ray beam 11 irradiates body 1 and is transmitted therethrough to a group 13 of ionization cells in the center of array 5. The angle of the X-ray fan beam is larger than the angle subtended by body 1 so that two peripheral sectors 15 of beam 11 are transmitted past the body without substantial attenuation to two groups of reference cells 17 at the periphery of the array. In a typical array, central group of cells 13 may, for example, comprise as many as 730 separate ionization detector cells, while each of the peripheral detector cell groups 17 may comprise a group of 6 cells. All 730 cells are active for studies of body regions, such as the abdomen and thorax. In head studies, the number is reduced to 512 active cells located centrally in group 13.

Each cell in the array is made up of a pair of positively charged anode plates 19 and a negatively charged cathode plate 21 interposed therebetween forming an ionization chamber. In operation, X-ray photons entering the ionization chamber interact with the xenon gas and ionize it to produce electron/ion pairs. The positively charged ions are collected at signal electrodes 21 and induce a signal current therein indicative of the X-ray intensity, while the electrons are collected at anodes 19. The electrical signal current obtained at each signal electrode 21 is produced predominantly by X-ray energy entering a single detector cell. In order to obtain X-ray attenuation data from many different angles (needed to reconstruct a CT cross-sectional image), the X-ray source and the detector array are caused, in one embodiment of scan geometries, to rotate jointly either clockwise or counterclockwise about the body, as suggested by arrows A and B in FIG. 1. In a typical CT scan, the X-ray source and the detector array are mounted in a gantry (not shown) and rotated jointly through a predetermined angle so as to obtain the needed projection data. U.S. Pat. Nos. 4,112,303 and 4,115,695 (both assigned to the same assignee as the present invention) disclose details of gantry construction. A preferred embodiment of the detector array is disclosed in U.S. Pat. No. 4,272,680, also assigned to the same assignee as the present invention. It should be noted that the method in accordance with the invention may be advantageously employed with various other CT scan geometries such as that, for example, known to those skilled in the art as the "fourth generation." Briefly, in this geometry, the detector comprises a stationary annular structure which surrounds part or all of the object to be studied, while the radiation source is caused to orbit the object to obtain measurements from a plurality of projection angles.

In the course of a scan, the output of each active detector cell is sampled by a data acquisition system 25, in one particular embodiment, 984 times, resulting in an equal number of projections or views. The sampling rate is cited only by way of example and may be larger or smaller, limited only by the Nyquist sampling criteria. The measurement in each projection obtained from a single detector cell represents, after preprocessing, a ray sum or line integral projection data corresponding to X-ray attenuation along a ray path through the object studied.

Referring again to FIG. 1, the raw projection data from the data-acquisition system (DAS) 25 is applied for preprocessing by a preprocessing computational unit 27. In a preferred embodiment, the preprocessing unit may be an array processor such as, for example, the one designated Model 100 available from Floating Point Systems (FPS) (Beaverton, Oreg.). This machine uses a 38-bit floating-point number representation with 28 of the 38 bits representing the mantissa. The manner in which the 38-bit word is structured is graphically illustrated in FIG. 3.

Figure 2:
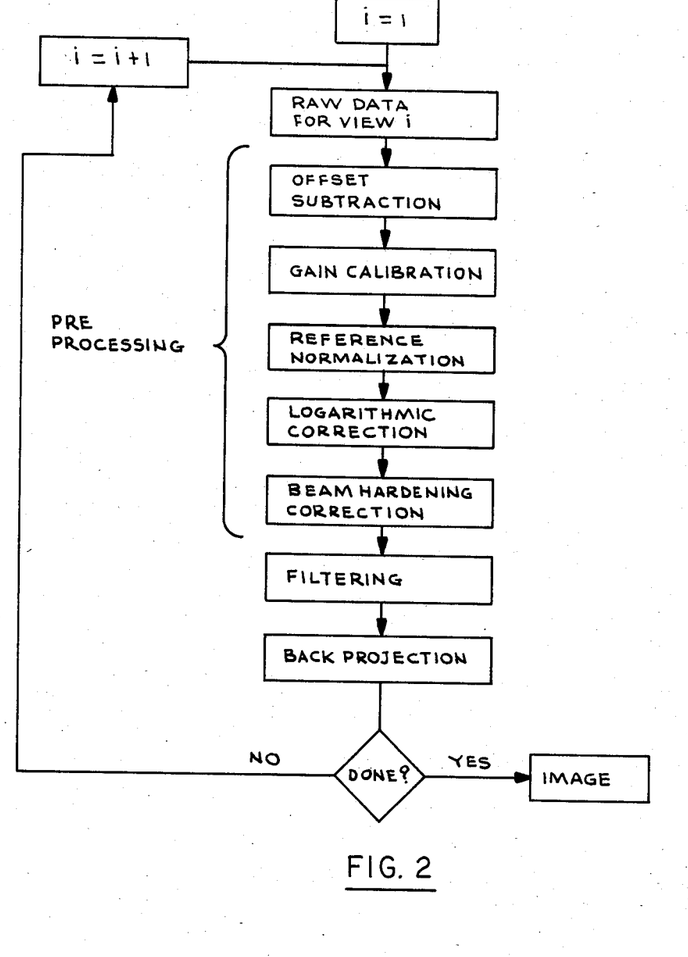
FIG. 2 depicts in flow-chart format the steps used in the preferred image reconstruction process and indicates steps of preprocessing, filtering and backprojecting.

The preprocessing steps carried out in processor 27 are summarized in flow-chart format in FIG. 2. Briefly, FIG. 2 shows steps typical of those used for transmission tomography. In this flow chart, "i" is the view index and reconstruction begins with preprocessing of the first view. Preprocessing begins with the step of offset correction needed to compensate for the fact that even without any X-ray excitation there may be what is called a "dark current" produced in the detectors or electronics. The offset correction step eliminates this current by subtracting it. Gain compensation is necessitated by the fact that each data channel, such as data-transmission channels 23 in FIG. 1 may have different gain due to the unequal sensitivity of the detector cells themselves, or due to the electronic gain variations. The reference-normalization step is utilized to compensate for the fact that the X-ray beam intensity during any given view can vary. The normalization is performed by monitoring the X-ray beam intensity by means of one or more of the reference detector cells 17 depicted at the periphery of detector 5 in FIG. 1. Alternatively, the intensity of the X-ray source may be monitored by detectors (not shown) positioned near collimator 9. The logarithmic-correction step generally follows the reference-normalization step in the preprocessing sequence of a transmission tomographic scanner. The step of beam-hardening correction, which follows the step of the logarithmic correction, is necessitated by the fact that X-rays are polychromatic so that the lower energy X-rays are preferentially absorbed. The transmitted X-rays are richer in high energies and become more penetrating or "harder" so that a uniform material appears progressively less dense. Such hardening, if uncorrected, may introduce an artifact known as "cupping" in the reconstructed images.

The preprocessing steps, as seen in FIG. 2, are followed by a step of filtering and backprojecting of the preprocessed data. In the preferred embodiment, the filtering operation requires convolving the preprocessed projection data with a kernel function prior to the operation of backprojection to create an image. Typically, the convolution operation is implemented by taking the discrete Fourier transform (DFT) of the preprocessed projection data, multiplying it by the DFT of the kernel function, and, finally, obtaining the filtered projection data by taking the inverse DFT (IDFT) of the product. It should be noted that DFT's are performed using a fast Fourier transform algorithm commonly denoted FFT.

In a conventional CT system, the preprocessing and filtering are both carried out in a single computational unit. Thus, in the conventional system the raw data from DAS 25 is preprocessed and filtered, respectively, in preprocessing unit 27 (FIG. 1) and filtration unit 37 which are implemented as one device, such as the FPS 100 array processer. The resulting line-integral projections are then applied to backprojector 31. The backprojected data can be displayed by any suitable means, such as a video display 33.

In some cases, it is desirable to preprocess the projection data in preprocessing unit 27 (FIG. 1) and perform the filtering operation in a filtration unit 37 comprised of an array processor, such as an FPS model XP22 or the like. This filtration unit is optimized for performing discrete Fourier transforms, but using a 22-bit floating point number representation with a 16-bit mantissa, as shown in FIG. 3.

More specifically, each data word in preprocessing unit 27 is stored in a 38-bit floating point format consisting of a 10-bit exponent and 28-bit mantissa. The exponent is structured as 1 sign bit and 9 magnitude bits, while the mantissa is structured as 1 sign bit and 27 magnitude bits. Each data word in filtration unit 37 is stored in a 22-bit floating point format consisting of a 6-bit (1 sign bit and 5 magnitude bits) exponent and 16-bit (1 sign bit and 15 magnitude bits) mantissa.

Figure 3:
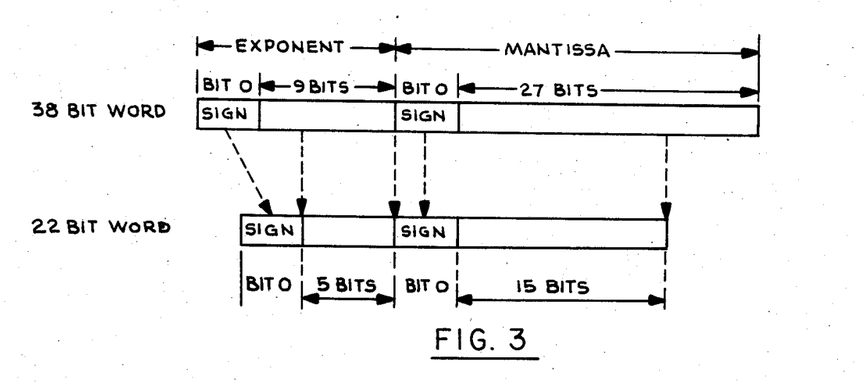
FIG. 3 illustrates graphically the bit distribution in a 38-bit word utilized in a high precision array processor and the bit distribution in a 22-bit word which is a truncated version of the 38-bit word.

FIG. 3 illustrates the restructuring of the data during the transfer from preprocessing unit 27 to filtration unit 37. The sign bits are transferred, the four most significant exponent bits are dropped and the twelve least significant mantissa bits are either truncated or rounded into the most significant mantissa bits. The dynamic range of the preprocessed data is such that the four most significant exponent bits are zero, so that dropping these bits does not cause any problems. However, the loss of the 12 mantissa bits reduces the accuracy. It is the use of number representations with reduced accuracy which causes errors to be added to the filtered projection data resulting in structured artifacts in the reconstructed image.

These artifacts can be reduced by utilizing a decorrelation process during the filtering process as carried out in the filtration unit. Prior to disclosing the detailed manner in which this is accomplished in accordance with the invention, it will be beneficial to consider some general principles pertaining to convolution using Fourier transforms, as well as DFT's and their use in performing convolution filtering.

Convolution of t-domain functions x(t) and y(t) will be considered first. The convolution operation can be denoted as $$z(t) = x(t) <*> y(t), \quad (1)$$

where function z(t) is the convolution of x(t) and y(t) and the symbol $<*>$ indicates the convolution operation. The function z(t) is given by $$z(t) = \int_{-\infty}^{\infty} x(t - \tau) y(\tau) d\tau. \quad (2)$$

The Fourier transform of function x(t) is denoted by X(f) and is defined by $$X(f) = \int_{-\infty}^{\infty} x(t) \exp(-j2\pi ft) dt, \quad (3)$$

where f is frequency, j is the square root of −1, and "exp" denotes a power of "e". The corresponding inverse Fourier transform is defined by:

$$x(t) = \int_{-\infty}^{\infty} X(f) \exp(j2\pi ft) df. \quad (4)$$

If Y(f) and Z(f) represent the Fourier transformations of y(t) and z(t), respectively, then it can be shown that:

$$Z(f) = X(f) Y(f). \quad (5)$$

Equation (5) indicates that the convolution of two signals can be evaluated in the Fourier domain using the following algorithm: (1) Take the Fourier transform of the first signal; (2) Take the Fourier transform of the second signal; (3) Multiply the Fourier transforms of the two signals; and (4) Take the inverse Fourier transform of the product.

In some cases when using a computer to do convolution, it is faster to use the Fourier transform approach instead of direct implementation of the convolution integral.

Consider a version of the signal x(t) displaced in "t" by "u". The shifted version is given by x(t−u). It can be shown that the Fourier transform of x(t−u) is given by:

$$x(t-u) <-> X(f) \exp(-j2\pi fu), \quad (6)$$

where the symbol $<->$ indicates a Fourier transform pair.

Now consider w(t), the convolution of x(t−u) and y(t). The Fourier transform of w(t), W(f), is given by the product of the transforms of x(t−u) and y(t). Using the results presented above, it can be shown that:

$$W(f) = X(f) Y(f) \exp(-j2\pi fu) = Z(f) \exp(-j2\pi fu). \quad (7)$$

After taking the inverse Fourier transform of Equation (7), the following is obtained:

$$w(t) = z(t-u). \qquad (8)$$

Thus, if one of the signals in a convolution is shifted by "u", then the resulting convolution will also be shifted by the same amount. The preceding material will now be related to an actual computer implementation.

Assume that a finite precision machine is used to form forward- and inverse-Fourier transforms. In the finite precision machine only a finite number of bits are used to represent a number. For example, numbers can be represented as fixed precision integers, block floating point, or floating point. The number words depicted in FIG. 3 used in the FPS100 and XP22 processors are in floating point format.

Because of the finite word length in the machine, all operations in the machine will have an error term built into the result. In general, the error is correlated with the input and might be multiplicative. However, for the purposes of this discussion, it will be assumed that the noise is additive and correlated to the input and the type of numerical operation performed on the input.

In a perfect machine, the Fourier transform of x(t) is given by X(f). In the finite precision machine, the Fourier transform of x(t), X'(f), will be given by:

$$X'(f) = X(f) + n(f;x), \qquad (9)$$

where n(f;x) is the frequency-dependent noise and the inclusion of "x" as a parameter implies that the noise depends on the input signal x(t).

Now consider convolution in the frequency domain using the finite precision machine. Let z'(t) be the convolution of x(t) and y(t) in a finite precision machine. The Fourier transform of z'(t), Z'(t) will be given by:

$$\begin{aligned} Z'(f) &= X'(f)\, Y'(f) \\ &= [X(f) + n(f;x)]\,[Y(f) + n(f;y)] \\ &\sim X(f)\, Y(f) + n(f;x,y) \\ &= Z(f) + n(f;x,y), \end{aligned} \qquad (10)$$

where it has been assumed in the above derivation that all of the truncation effects can be combined into one term. The t-domain version of Z'(f), z'(t), is given by the following when the finite precision machine is used to perform the inverse Fourier transform:

$$z'(t) = z(t) + m(t;\, x, y), \qquad (11)$$

where m(;) is additive noise that depends on the input signals "x" and "y", the characteristics of the processor, and the intermediate noise term n(;).

Now consider the use of the above equations in the filtration/convolution step used in the standard filtered back-projection algorithm. Let x(t;α) be an angle-dependent preprocessed projection where α is the angle of the view. Let y(t) be the convolution kernel. Then the convolution of the projection with the kernel will be given by:

$$z(t;\alpha) = x(t;\alpha) <*> y(t). \qquad (12)$$

In the finite precision machine z'(t,α), given by the following, will be obtained:

$$z'(t,\alpha) = z(t) + m(t;x(\alpha),y). \qquad (13)$$

Assume that the object from which the projections were obtained is circularly symmetric. In this situation, the projections will be independent of view angle and, hence, the noise term due to the finite precision machine, m(;), will be independent of view angle. Thus, the noise is highly correlated from view to view. It is well known that correlated noise in the projections will generate rings and center spots, if the data is reconstructed with a standard filtered backprojection reconstruction algorithm.

Referring again to the convolution of shifted signals, discussed hereinbefore, assume that the view-dependent projection is shifted by an amount that is also a function of the view angle. The shifted projection, p(t), is given by:

$$p(t;\alpha) = x(t - u(\alpha); \alpha). \qquad (14)$$

The Fourier transform of p(t;α), P(f,α), is given by the following:

$$P(f;\alpha) = X(f;\alpha)\, \exp(-j2\pi f u(\alpha)). \qquad (15)$$

The Fourier transform of p(t;α), P'(f;α), using the finite precision processor, is given by:

$$\begin{aligned} P'(f;\alpha) &= P(f;\alpha) + n(f;p(\alpha)) \\ &= P(f;\alpha) + n(f;x(\alpha),\, u(\alpha)). \end{aligned} \qquad (16)$$

It is seen from Equation (16) that the noise will also be correlated with the shift u(α). Therefore, if the projections are shifted randomly or pseudo-randomly from view to view, then the noise becomes uncorrelated because the noise is correlated with the shift. If the shifted version is used to find the filtered projection, then a shifted filtered projection will be obtained, but with noise that is uncorrelated with the view angle. This is then a general method in accordance with the invention to decorrelate the noise that originates from the finite word lengths in a finite precision Fourier transform unit.

Some of the general principles of discrete Fourier Transforms will be discussed next.

In any digital implementation of a filtering process, only samples of the functions that are to be convolved are used by the processor. Consider the signal x(t) used in the discussion above. Assume that it is sampled at equal intervals $\delta_t$ apart and that a sample is taken at the origin in "t"-space. Then the samples of x(t), $x_i$, i = $-\infty$, ..., $\infty$, are related to the original function as follows:

$$x_i = x(i\delta_t), \text{ for } i = -\infty, \ldots, \infty. \qquad (17)$$

The numerical Fourier transform (NFT) of the samples x(i), Xn(f), is given by:

$$Xn(f) = \sum_{i=-\infty}^{\infty} x_i \exp(-j2\pi i\, \delta_t f). \qquad (18)$$

It can be shown that the NFT of the samples can be related to the Fourier transform of original unsampled data as follows:

$$Xn(f) = (1/\delta_t) \sum_{h=-\infty}^{\infty} X(f - h/\delta_t). \quad (19)$$

The Nyquist theorem is clearly seen in this equation. If X(f) is zero for $|f| > 0.5/\delta_t$, then X(f) can be recovered from Xn(f).

In practice the signal is spatially limited so that x(t)=0 outside of some finite interval. For purposes of discussion, assume that x(t)=0 outside of the interval [0,T]. Thus, there will be only $N=T/\delta_t$ non-zero samples of the function.

In practice, it is also desired to compute only the Fourier transform of the signal at a finite number of samples. Assume that N frequency samples are also desired at intervals $\delta_f=1/T$. The samples of Xn(f), $X_k$, k=0, 1, ..., N−1, are related to the original Xn(f) function as follows:

$$X_k = Xn(k\delta_f). \quad (20)$$

The previous results can be combined to obtain what is known as the discrete Fourier transform (DFT) of $x_i$:

$$X_k = \sum_{i=0}^{N-1} x_i \exp(-j2\pi ik/N). \quad (21)$$

for k=0, 1, ..., N−1. It can be shown that the inverse DFT (IDFT) is given by:

$$x_i = 1/N \sum_{k=0}^{N-1} X_k \exp(j2\pi ik/N). \quad (22)$$

In general, on the order of $N^2$ operations are needed to perform a DFT or an IDFT. If N is a power of two, then the DFT and IDFT of a signal can be computed using on the order of N log N operations. Such an implementation is also known as a radix-2 fast Fourier transform (FFT).

Now consider convolution in a sampled space. It is desired to convolve the signals x(t) and y(t) using just samples of the functions. The sampled functions are given by $x_i$ and $y_i$, respectively, where i=0,1...N−1. Assume the Nyquist criterion is satisfied for both functions. Then the following can be derived:

$$z_i = \delta_t \sum_{h=0}^{N-1} x_{(i-h)} y_h, \quad (23)$$

where $z_i$ is a sampled version of $z(t)=x(t)<*>y(t)$. It can be shown that $z_i$ is zero outside of the interval [0,2N−1]. It is seen that when two signals of length N are convolved, then the output will have length 2N−1.

Consider the DFTs of $x_i$ and $y_i$, $X_k$ and $Y_k$, respectively. Then it can be shown that the IDFT of the product of $X_k$ and $Y_k$, denoted by $g_i$ is given by:

$$g_i = IDFT(X_k Y_k) \quad (24)$$

$$= \sum_{h=0}^{N-1} x_{(i-h)/N} y_h, \, i = 0, 1, ..., N-1,$$

where the operation a|b means "a" modulo "b". It will be seen that there are three differences between the convolutions used to obtain $g_i$ and $z_i$. They are:

(1) They differ by the scale factor $\delta_t$.

(2) $g_i$ is defined for the range [0,N−1] instead of [0,2N−1] for $z_i$. However, it appears that $g_i$ is defined over a subset of the range defined for $z_i$.

(3) $z_i$ is obtained using regular convolution and $g_i$ is obtained using circular convolution. The difference comes about because of the modulo-N operation found in the definition of $g_i$. This operation implies that values of $x_i$ outside of the range of [0,N−1] will be evaluated by using the value of $x_i$ after evaluating the original index modulo-N. This can be contrasted to the definition of $z_i$ where it can be seen that values of $x_i$ outside of the range [0,N−1] are assumed to be zero.

It can be shown that normal convolution can be obtained by using circular convolution if the signals are padded with zeros prior to circular convolution. Padding with zeros implies augmenting at least one of the signals with at least N−1 zeros prior to performing circular convolution. Zero padding, in effect, causes values of signal outside of the range [0,N−1] to be zero. It turns out that it does not matter how the signal is augmented with zeros. Zeros can be prepended to the signal; appended to the signal; or a mixture—some at the beginning and some at the end. The origin of the convolved signal will always be at the same location as the origin of the inputted signals as is evident from Equation (8). However, each type of zero-padding will cause a different type of phase in the DFT of the zero-padded signal, as indicated in Equation (6). It will be appreciated that, by varying the type of zero-padding, the phase of the DFT of the inputted signals can be varied. This in fact is what is required to decorrelate the noise that is introduced by a finite precision processor, as will be appreciated from comments following Equation (13). Because zero-padding is already used to avoid circular convolution artifacts and the locations of the zeros used for zero-padding can be varied, the random shift in the input signal required to avoid correlated noise in accordance with the invention can be obtained readily through modification of the zero-padding technique.

The process by which the zero-padding is implemented in accordance with the invention in a CT system to decorrelate the noise will now be disclosed next with reference to FIG. 1. In general, the raw projection data collected by the data acquisition system 25 is preprocessed by preprocessor 27 to generate line-integral projection data. The DFT of the kernel function required by the reconstruction algorithm is then taken in the filtration unit 37. The preprocessed projections are zero-padded and filtered with the kernel function in filtration unit 37. The filtered projection is passed to backprojector 31 and backprojected into an image matrix which can be displayed on display 33. The process is repeated for all views.

Figure 4:
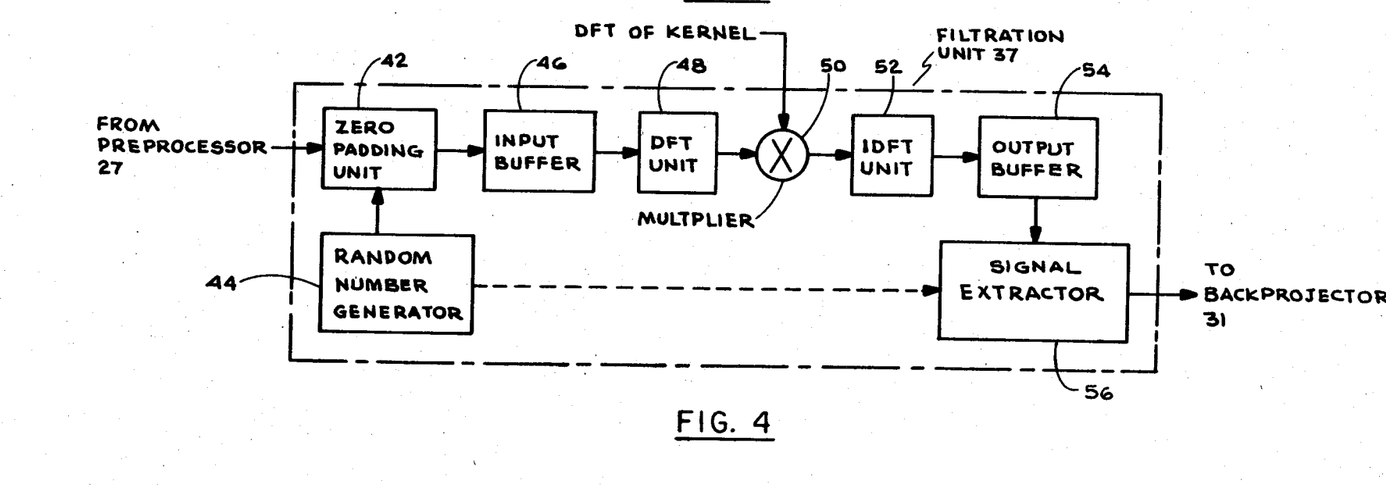
FIG. 4 illustrates in functional block diagram form the filtration unit in accordance with the invention needed to reduce artifacts due to truncation errors.

The detailed manner in which zero-padding is achieved will now be disclosed with reference to FIG. 4 which depicts in functional block form filtration unit 37 previously disclosed hereinbefore with reference to FIG. 1. The preprocessed projection data is applied to a zero-padding unit 42 connected to receive a random or pseudo-random integer number, v, generated by a random number generator 44. The number of zeros either prepended or appended to the preprocessed data is thus randomly determined by the number "v". It will be assumed, for the purpose of describing one exemplary embodiment that an input buffer 46 is preset to zero. Then the preprocessed data is transferred to the input buffer starting at location "v." It will be recognized that in another embodiment, the preprocessed data can be transferred to the input buffer starting at location "v" and the input buffer set to zero at locations before "v" and after V+N, where N is the number of detectors. For large values of "v" there will not be enough locations in the buffer to accommodate the entire projection. The projection portion which cannot be accommodated is "wrapped-around" so that the unaccommodated portion is inserted at the beginning of the buffer.

The length of the input buffer in a preferred embodiment is selected to be $M=2^m$, where M is greater than $2N-1$; where N is the number of detectors (512 or 730), and where "m" is an integer. In some cases, such as in high-resolution reconstructions or preinterpolation schemes for minimizing backprojection interpolation artifacts, "M" is doubled or quadrupled. The DFT of the zero-padded projection is then taken by a DFT unit 48 and multiplied in a multiplier 50 with the DFT of a kernel function. The IDFT of the product is taken in an IDFT unit 52 to obtain a filtered projection which is then transmitted to an output buffer 54. The filtered projection is extracted from the output buffer by a signal extractor unit 56 starting at location "v" provided to the output buffer by random number generator 44. The extracted projection is then applied to backprojector 31 (FIG. 1). It will be recognized that the extraction operation could also be performed in the backprojector. In such an embodiment the random number "v" is passed to the backprojector as a synchronization signal.

All of the remaining projections are similarly processed using a different random number. In this manner, the truncation errors will be different for each projection, so that during backprojection the errors will be decorrelated thereby avoiding center spot and ring artifacts in the reconstructed image.

In the embodiment described above, the starting data address within the buffer was selected randomly. However, it should be recognized that it could also be selected using a deterministic function of the view number. A triangle, of which a ramp is a special case, is an example of such a function. In this case, the preprocessed data is placed at the beginning of the buffer for the first view. The starting address is increased by one for the successive views.

The preferred embodiment of the invention has been disclosed hereinbefore with reference to a CT system, wherein the random shift in the projection data is accomplished by variations of the zero-padding technique. It will be recognized, however, that if a projection with zeros appended is considered to be one signal, then the random positioning within the input buffer can be accomplished by rotational permutation of the zero-padded projection. That is, the signal can be shifted an arbitrary number of positions in a given direction within the buffer, while the data being forced out of the buffer is reapplied to the opposite end of the buffer. For example, if the signal is shifted left to right, then the signal forced out of the right side is reapplied as an input signal to the left side of the buffer input.

The preferred embodiment of the invention has been disclosed hereinbefore with reference to preprocessed projection data with appropriate zero-padding. In applications other than CT, a plurality of input signals, produced by one or more transducers, can be convolved with a kernel function. One such application, by way of example and not limitation, is in seismology where a plurality of input signals are produced by seismic sensors. The signals are then convolved with a kernel to, for example, enhance signal-to-noise characteristics or to deconvolve degradation functions. In this situation, if the input signals are similar, then filtration truncation errors in the resulting output signals will become correlated. It will be recognized that the invention as disclosed is not limited to CT projection data, but is applicable to situations such as seismology, or other diagnostic modalities, to decorrelate filtration truncation errors.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. A device for convolving a plurality of input signals, which signals are provided by transducer means, with a common kernel by taking the inverse discrete Fourier transform (IDFT) of the product of the discrete Fourier transform (DFT) of each of said input signals with the DFT of a common kernel using a finite precision machine, wherein as a result of using the finite precision machine the resulting convolved signals have correlated noise, said device comprising:
   means for obtaining the DFT of each signal forming part of said plurality of input signals;
   means for obtaining a product of the DFT of each of said input signals and the DFT of said kernel;
   means for taking the IDFT of said product; and
   means for decorrelating the correlated noise, said decorrelating means including means for performing a rotational permutation operation on each of said input signals prior to obtaining the discrete Fourier transforms thereof, wherein the degree of rotational permutation is selectively variable for each of the input signals.

2. The device of claim 1 wherein the discrete Fourier transforms of said input signals are obtained using fast Fourier transform (FFT) methods.

3. The device of claim 2 wherein the DFT of each of said input signals is obtained using radix-2 Fourier transforms.

4. The device of claim 1, 2 or 3 further comprising random number generator means, wherein the degree of rotational permutation of said input signals is determined based on numbers generated by said random number generator means.

5. The device of claim 1, 2 or 3 wherein the degree of rotational permutation is determined using a deterministic function.

6. The device of claim 5 wherein said deterministic function comprises a triangular function.

7. The device of claim 5 wherein said deterministic function comprises a sinusoidal function.

8. The device of claim 1 wherein said means for decorrelating comprises zero-padding means, wherein rotational permutation is performed by zero-padding said input signals.

9. The device of claim 8 wherein said zero-padding means further comprises an input buffer wherein zero-padding is accomplished by positioning said input signals at predetermined locations within said buffer.

10. The device of claim 9 wherein said input buffer is zeroed prior to positioning said input signals therein.

11. The device of claim 9 wherein said input buffer is zeroed after positioning said input signals therein.

12. The device of claim 9, 10, or 11 further comprising random number generator means, the random number outputs of which are used to randomly position each of said input signals within said input buffer.

13. The device of claim 12 further comprising extractor means synchronized with said random number generator means for extracting the convolved signals.

14. The device of claim 9, 10 or 11 wherein the position of each input signal within the input buffer is determined using a deterministic function.

15. The device of claim 14 wherein said deterministic function comprises a triangular function.

16. The device of claim 14 wherein said deterministic function comprises a sinusoidal function.

17. The device of claim 1, wherein said input signals comprise line integral projection data representative of characteristics of an object under examination.

18. A device for reconstructing into intelligible form line-integral projection data created by a radio frequency, ultrasound, X- or gamma radiation, transmitted or emitted from a plurality of positions through an object to be inspected and onto detector means whereat a multiplicity of input signals are received and detected, said device including finite precision means for convolving said signals with a common kernel by taking the inverse discrete Fourier transform (IDFT) of the product of discrete Fourier transform (DFT) of said input signals and said kernel function, wherein as a result of using the finite precision means the resulting convolved signals have correlated noise, said means for convolving comprising:

means for obtaining the DFT of each of said input signals;

means for obtaining a product of the DFT of each of the input signals and the DFT of the kernel;

means for taking the IDFT of said product; and means for decorrelating the correlated noise, said decorrelating means including means for performing a rotational permutation operation on each of said input signals prior to obtaining the discrete Fourier transforms thereof, wherein the degree of rotational permutation is selectively variable for each of the input signals.

19. The device of claim 18 wherein the discrete Fourier transforms of said input signals are obtained using fast Fourier transform (FFT) methods.

20. The device of claim 19 wherein the DFT of each of said input signals is obtained using radix-2 Fourier transforms.

21. The device of claim 18, 19 or 20 further comprising random number generator means, wherein the degree of rotational permutation of said input signals is determined based on numbers generated by said random number generator means.

22. The device of claim 18, 19 or 20 wherein the degree of rotational permutation is determined using a deterministic function.

23. The device of claim 22 wherein said deterministic function comprises a triangular function.

24. The device of claim 22 wherein said deterministic function comprises a sinusoidal function.

25. The device of claim 18 wherein said means for decorrelating comprises zero-padding means, wherein rotational permutation is performed by zero-padding said input signals.

26. The device of claim 25 wherein said zero-padding means further comprises an input buffer and wherein zero-padding is accomplished by positioning said input signals at a predetermined location within said input buffer.

27. The device of claim 26 wherein said input buffer is zeroed prior to positioning said input signal therein.

28. The device of claim 26 wherein said input buffer is zeroed after said input signal is positioned therein.

29. The device of claim 26, 27, or 28 further comprising random number generator means, the random number outputs of which are used for randomly positioning each of said input signals within said buffer.

30. The apparatus of claim 29 further comprising extractor means synchronized with said random number generator means for extracting the convolved signals.

31. The device of claim 26, 27, or 28 wherein the position of each of said input signals is determined using a deterministic function.

32. The device of claim 31 wherein said deterministic function is selected to be a triangular function.

33. The device of claim 31 wherein said deterministic function is selected to be a sinusoidal function.

34. The device of claim 26 wherein the discrete Fourier transforms of said input signals are obtained using fast Fourier transform methods.

35. The device of claim 34 wherein the length of the input buffer is selected to be a power of 2.

36. The device of claim 18 wherein said line-integral projection data is created by a fan beam of X- or gamma radiation transmitted or emitted from a plurality of positions through an object to be inspected.

* * * * *

UNITED STATES PATENT AND TRADEMARK OFFICE
CERTIFICATE OF CORRECTION

PATENT NO. : 4,606,004

DATED : Aug. 12, 1986

INVENTOR(S) : Carl R. Crawford and Kishore C. Acharya

It is certified that error appears in the above-identified patent and that said Letters Patent is hereby corrected as shown below:

Col. 9, line 62, Equation (24), change " $= \sum_{h=0}^{N-1} x_{(i-h)}/N^y h$ "

to -- $= \sum_{h=0}^{N-1} x_{(i-h)} | N^y h$ --

Signed and Sealed this

Thirty-first Day of March, 1987

Attest:

DONALD J. QUIGG

Attesting Officer

Commissioner of Patents and Trademarks